US005095758A

United States Patent [19]
Cox et al.

[11] Patent Number: 5,095,758
[45] Date of Patent: Mar. 17, 1992

[54] WATER CUT MONITORING MEANS AND METHOD

[75] Inventors: Percy T. Cox; Theodore W. Nussbaum; Charles L. Gray, Jr., all of Houston, Tex.

[73] Assignee: Texaco Inc., White Plains, N.Y.

[21] Appl. No.: 619,621

[22] Filed: Nov. 29, 1990

[51] Int. Cl.⁵ .................... G01F 1/74; G01R 27/22
[52] U.S. Cl. ............... 73/861.04; 73/61.1 R; 324/444; 324/694
[58] Field of Search ............. 73/861.04, 61.1 R; 324/444, 446, 664, 687, 689, 683, 693, 694, 709

[56] References Cited
U.S. PATENT DOCUMENTS

| | | | |
|---|---|---|---|
| 4,751,842 | 6/1988 | Ekrann et al. | 73/861.04 X |
| 4,774,680 | 9/1988 | Agar | 73/861.04 X |
| 4,974,446 | 12/1990 | Vigneaux | 73/861.04 X |
| 5,033,289 | 7/1991 | Cox | 73/61.1 |

Primary Examiner—Herbert Goldstein
Attorney, Agent, or Firm—Robert A. Kulason; James J. O'Loughlin; Ronald G. Gillespie

[57] ABSTRACT

The present invention is a water cut monitor which includes a settling tank in which a quantity of fluid from a producing well is accumulated. The fluid is removed as a stream of fluid after a predetermined interval from the accumulation of the fluid by the settling tank so as to allow the accumulated fluid to separate into three phases: free water, water-continuous and oil-continuous. The flow rate of the stream of fluid is measured and a corresponding flow rate signal is provided as well as a temperature signal corresponding to a sensed temperature of the stream of fluid. The water cut monitor includes a plurality of electrodes in contact with the fluid. Injection electronics connected to at least one of the electrodes provides an injection voltage and injection current to the fluid stream and also provides signals corresponding to the injection voltage and injection current. A voltage in the fluid stream is measured and a measurement signal provided. A computer determines the water cut of the petroleum stream in accordance with the temperature signal, the injection voltage and injection current signals, the electrical phase angle signal and the measured voltage signal.

32 Claims, 3 Drawing Sheets

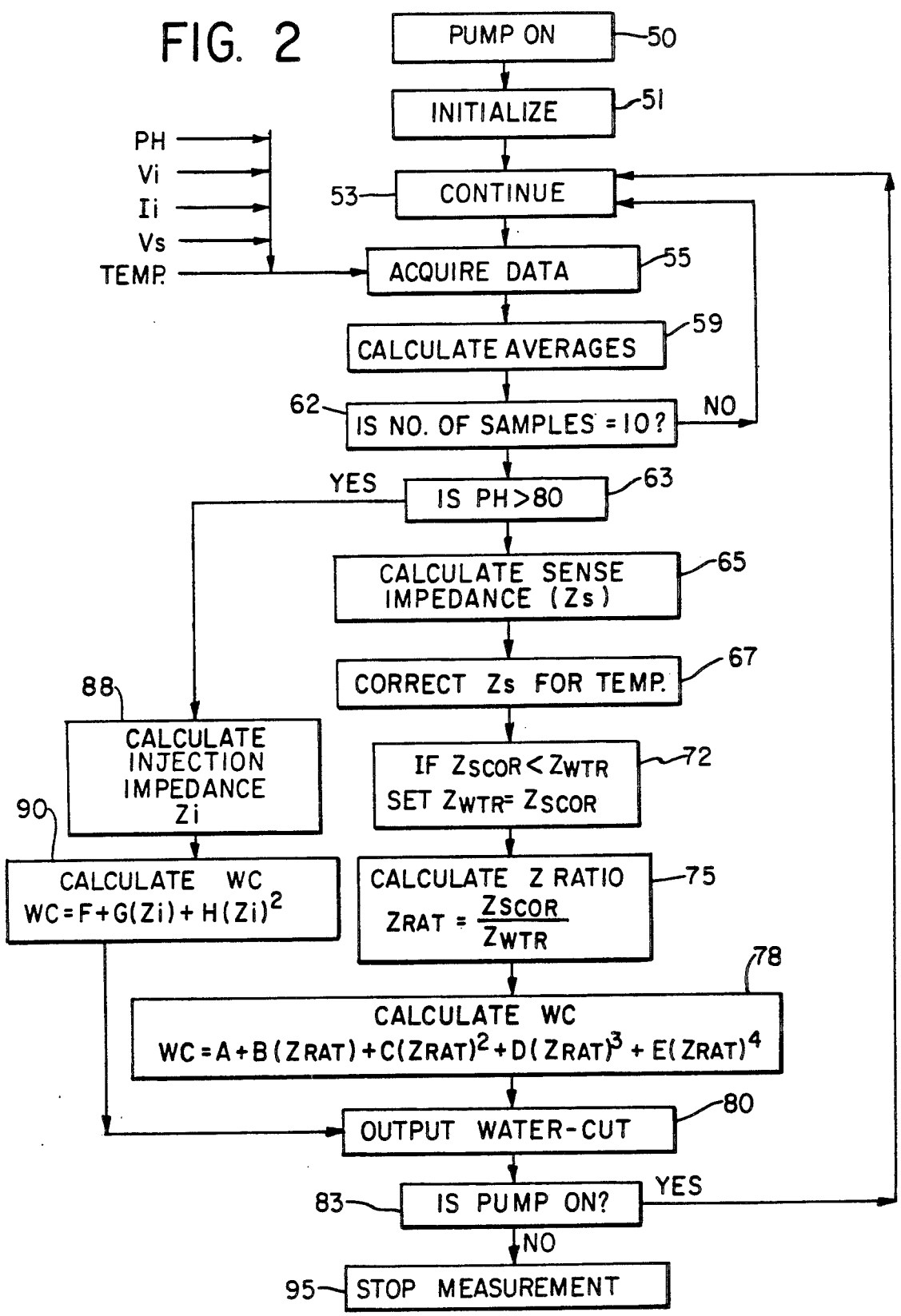

5,095,758

WATER CUT MONITORING MEANS AND METHOD

BACKGROUND OF THE INVENTION

Field of the Invention

The present invention relates to monitors in general and, more particularly, to water cut monitors.

SUMMARY OF THE INVENTION

The present invention is a water cut monitor which includes a settling tank in which a quantity of fluid from a producing well is accumulated. The fluid is removed as a stream of fluid after a predetermined interval from the accumulation of the fluid by the settling tank so as to allow the accumulated fluid to separate into three phases: free water, water-continuous and oil-continuous. The flow rate of the stream of fluid is measured and a corresponding flow rate signal is provided as well as a temperature signal corresponding to a sensed temperature of the stream of fluid. The water cut monitor includes a plurality of electrodes in contact with the fluid. Injection electronics connected to at least one of the electrodes provides an injection voltage and injection current to the fluid stream and also provides signals corresponding to the injection voltage, injection current and the phase angle between the injection voltage and injection current. A voltage in the fluid stream is measured and a measured voltage signal provided. A computer determines the water cut of the petroleum stream in accordance with the temperature signal, the injection voltage, the electrical phase angle and injection current signals and the measured voltage signal.

The objects and advantages of the invention will appear more fully hereinafter, from a consideration of the detailed description which follows, taken together with the accompanying drawings wherein two embodiments are illustrated by way of example. It is to be expressly understood, however, that the drawings are for illustrative purposes only and are not to be construed as defining the limits of the invention.

DESCRIPTION OF THE DRAWINGS

FIG. 2 is a flow diagram of the operation of the water cut monitoring means shown in FIG. 1.

DESCRIPTION OF THE INVENTION

Oil field production is defined in terms of barrels of oil per day (BOPD) and barrels of water per day (BWPD). These figures are determined by the measurement of flow rate and water cut. Many commercial flowmeters are available which yield satisfactory flow values. A number of commercial water cut meters are also available. Most of these meters, however, are designed for use only when the oil/water mixture is oil continuous, i.e., when any water present is suspended within the oil. These meters function purely as a capacitance measurement and operate properly only when a non-conductive (high impedance) path exists across the measurement electrodes. In water-continuous emulsions, a conducting path exists across the probe which essentially "shorts out" the capacitance measurement. The shorting effect is highly sensitive to salinity and temperature changes and renders standard capacitance probes useless in water-continuous operation when only a small amount of salt is present. The present invention is inexpensive and can operate over the entire 0 to 100 percent range of water cut, even where high water salinities and heavy oil emulsions are encountered.

Figure 1:
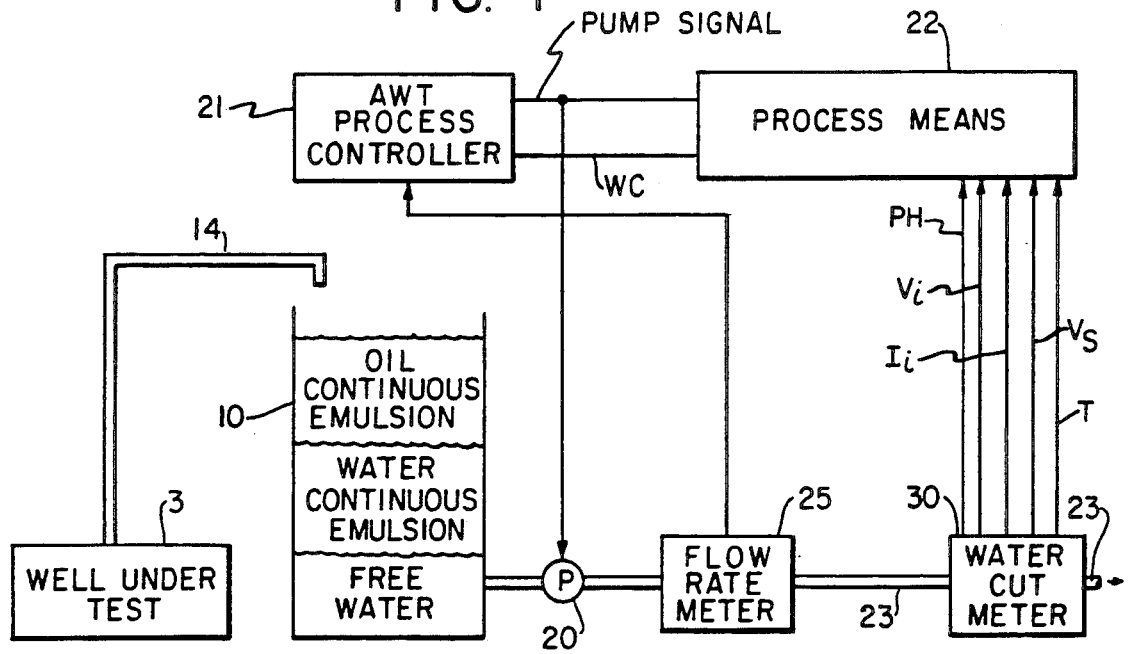
FIG. 1 is a drawing of a water cut monitoring means and method constructed in accordance with the present invention.

With reference to FIG. 1, there is shown a well under test 3 providing a production stream to the settling tank 10 via line 14. After a predetermined quantity of the production stream has entered settling tank 10, further filling of settling tank 10 is stopped. Over a predetermined period of time the fluid in settling tank 10 will partially separate to provide free water at the bottom of the tank 10; above this, the water-continuous emulsion exists, and finally at the top of tank 10 the fluid is an oil-continuous emulsion. After the predetermined period of time has elapsed, a pump 20, controlled by the AWT process controller 21, pumps the fluid from the bottom of tank 10 through a flowmeter 25 and thence through a water cut meter 30, and finally discharges the fluid to the production system, all via a line 23.

Water cut meter 30 provides five signals to process means 22: the injection voltage $V_i$, the injection current $I_i$, the phase angle PH, the sensed voltage $V_s$, and the temperature T. The obtaining of those signals and their utilization will be explained more fully hereinafter.

Initial fluid pumped from the bottom of tank 10 is practically always water. The water cut system of the present invention measures the impedance of the water (Z water) and retains this value. When the water-continuous emulsion begins to flow through water cut meter 30 the impedance (Z emulsion) increases. Dividing Z emulsion by Z water gives Z ratio, which is proportional to the percent water cut of the water-continuous emulsion. When the emulsion switches to the oil-continuous phase, the electrical phase angle between $V_i$ and I increases dramatically. This increase is used to change the measurement method to an inverse relationship between the injection impedance and percent water cut. The present invention can switch back and forth between oil and water-continuous phases with no loss of accuracy. In the event no free water is present in tank 10, a default value of Z water typical of low water wells is assigned.

Referring to FIG. 2, which is a flow chart, block 50 represents pump 20 being turned on by the pump signal. The pump signal is used to initialize all the coefficients of values required for all calculations as represented by block 51 entitled "INITIALIZE". The following values are initialized: water-continuous equation coefficients A, B, C, D and E; oil-continuous equation coefficients F, G and H; sensed impedance constant KA; temperature curve coefficients AA, BB, and water impedance initial value SWINIT.

From block 51 we go to block 53 entitled "CONTINUE MODE" which means process means 22 continues to the next step which is block 55. Block 55, entitled "ACQUIRE DATA", represents the acquisition of data signals $V_i$, $I_i$, PH, $V_s$ and temperature. Block 59 is the next step which calculates averages of the acquired data. From block 59 we proceed to block 62 which raises the question: is number of samples ten? If the answer is no, the system is recycled back to "CONTINUE" block 53 and measurements made again and the calculation goes on again until ten samples are collected and averaged, at which point block 62 provides a "yes" answer to block 63 which asks "is the phase angle greater than 80 degrees?" If PH>80 the fluid is oil-continuous and block 88 is used to calculate the injection impedance $Z_i$ and block 90 calculates water cut using the equation:

$$WC = F + G(Z_i) + H(Z_i)^2 \qquad 1.$$

If PH<80, block 65 calculates sense impedance as:

$$Z_s = (V_s/I_i) \times KA \qquad 2.$$

$Z_s$ is then corrected for temperature change using the equations:

$$Z_s cpr = Z_s + KB \times Z_s \times (DEGC - 40) \qquad 3.$$

$$DEGC = AA + BB \times Temp \qquad 4.$$

All of this is represented by block 67 entitled "Correct $Z_s$ for temperature". From block 67 we proceed to block 72 which makes the statement: If $Z_s$ corrected is less than Z water, set Z water equal to $Z_s$ corrected. This procedure determines the water impedance Z water to be the lowest impedance measurement. If $Z_s$ corrected is greater than Z water, the value of Z water is not changed and the next step is represented by block 75 entitled "Calculate Impedance Ratio Zrat". Zrat equals Zscor/Zwater. Finally as represented by block 78, the value of Zrat is used to calculate the water cut of the water-continuous fluid in accordance with the following equation 5:

$$WC = A + B(Zrat) + C(Zrat)^2 + D(Zrat)^3 + E(Zrat)^4 \qquad 5.$$

This calculated value WC is provided by process means 22 in the form of signal WC to the AWT process controller 21.

Block 83 inquires if the pump is still on. If so, the processor loops back to block 53 where a new measurement begins. If the pump haqs gone off the measurement process is halted (block 95).

Coefficients for the water-continuous water cut equation are empirically determined by recording values of Zrat as fluid samples are taken. Samples are then analyzed to determine the actual percentage water cut. A plot of water cut WC versus Zrat is then made using computer curve-fitting software. This software can curve fit the plotted points and give the coefficients of the resultant polynomial curve. Data are taken for several different water salinities and a curve is determined which best fits all the data points. Coefficients from this curve are then used in the water-continuous polynomial equation.

Coefficients for the oil-continuous water cut equation are determined in a similar manner by simultaneously recording values of the injection impedance, Zi, and taking water cut samples when the emulsion is known to be oil-continuous. A curve fit for the WC versus Zi data is then obtained from the curve-fitting program and the coefficients determined. These coefficients are then entered into oil-continuous WC equation 1.

Figure 3:
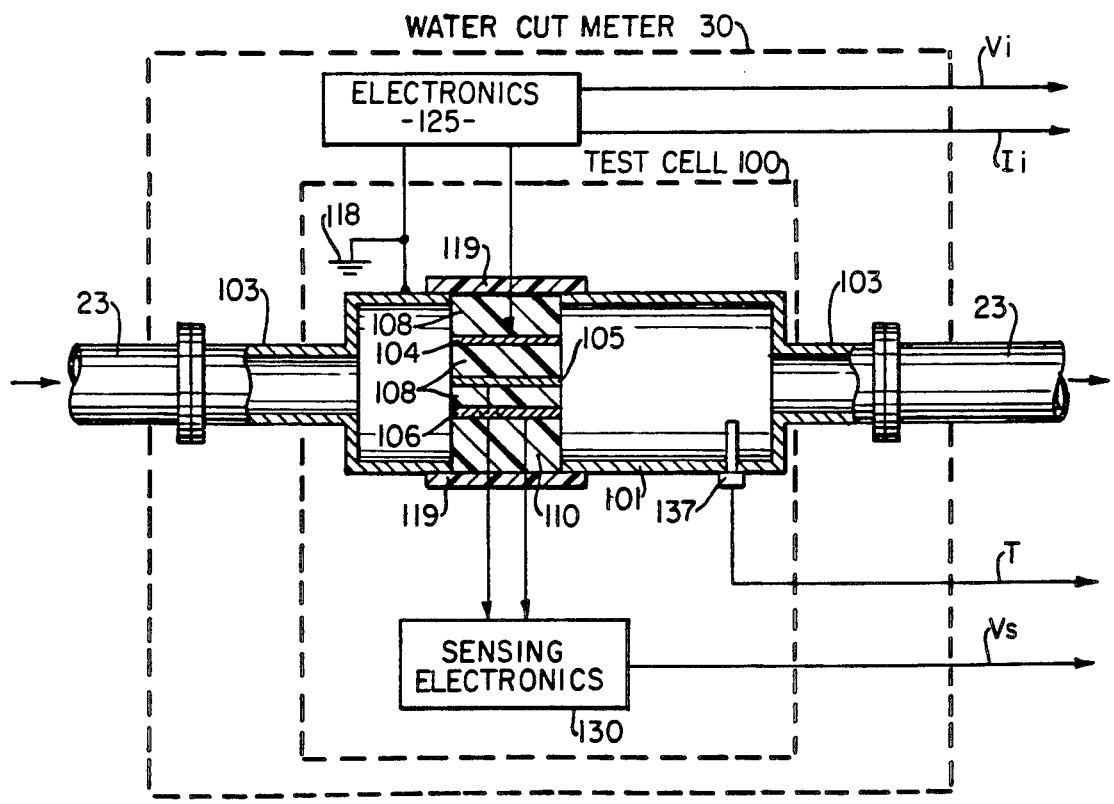
FIG. 3 is a partial simplified block diagram and a partial schematic diagram of one embodiment of the water cut meter shown in FIG 1.

In one embodiment of the present invention, water cut meter 30 is arranged as shown in FIG. 3. Test cell 100 includes a housing 101 with flow line adapter pipes 103. Housing 101 has a square cross-section to the fluid flow. Flow line adapters 103 permit connecting of housing 100 to line 23. Test cell 100 also contains three electrodes 104, 105, and 106, mounted along with insulator 108 to form a sensing body 110 having end caps 111. Excitation electronics 125 is connected between ground 118 and electrode 104.

Excitation electronics 125 has within it an oscillator which provides an AC injection voltage across to an electrode 104 and ground 118 causing an injection current to flow within the fluid. Although the injection voltage in the present invention may be used at substantially lower frequencies or at higher frequencies, a preferred frequency range is from 1 MHz to 50 MHz. Also within excitation electronics 125 is circuitry that provides signals $V_i$ and $I_i$, corresponding to the injection voltage and the injection current, respectively. The injection signal provided to electrode 104 creates an electric field within the fluid. Electrodes 105 and 106 are electrically connected to sensing electronics 130 which senses the voltage picked up across electrodes 105 and 106 and provides a corresponding signal Vs. A temperature sensor 137 senses the temperature of the fluid flowing in housing 23 and provides a corresponding temperature signal T.

Figure 4:
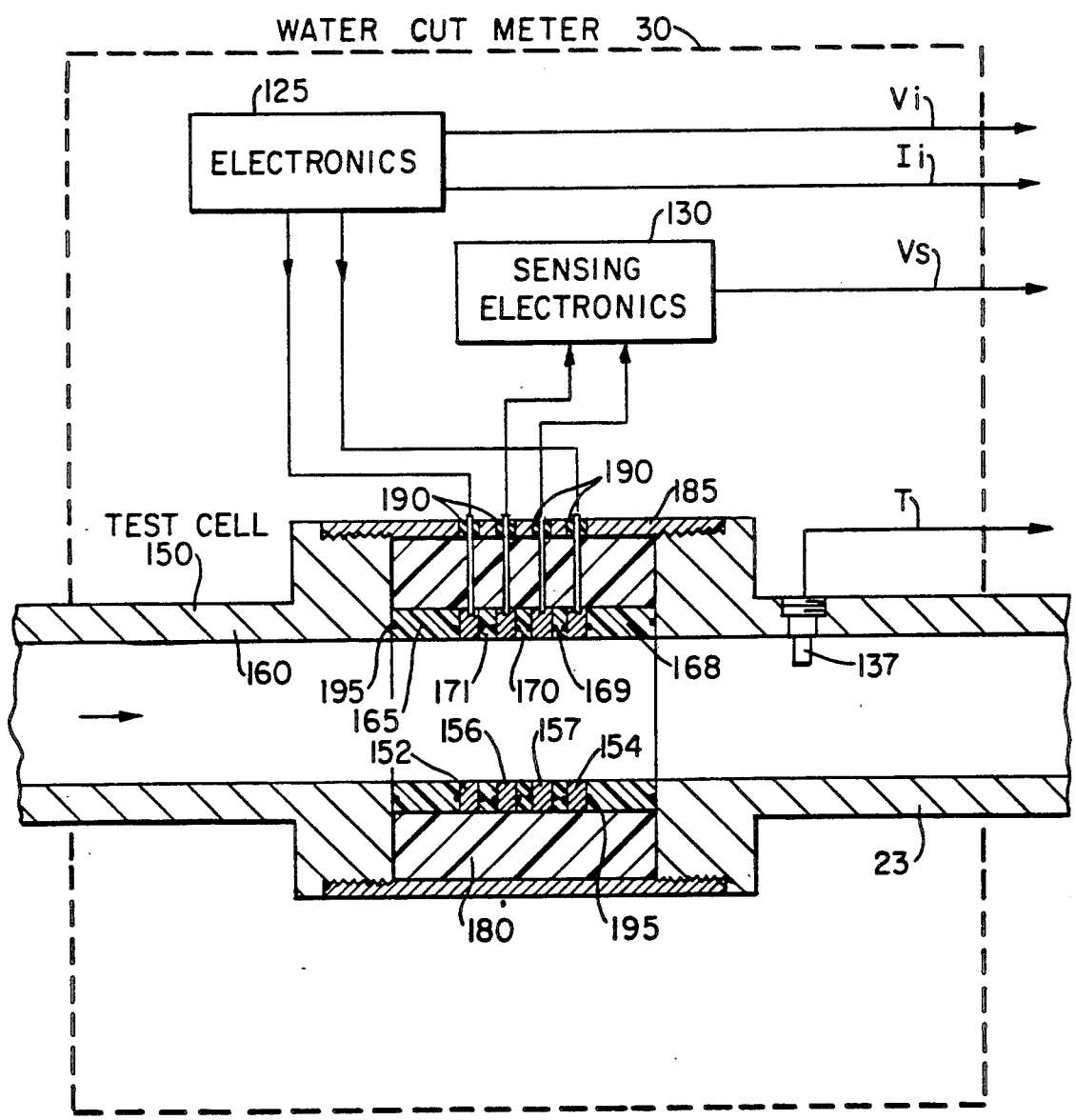
FIG. 4 is a partial simplified block diagram and a partial schematic diagram of another embodiment of the water cut meter shown in FIG. 1.

Referring now to FIG. 4 there is shown another embodiment of water cut meter 30 which is non-intrusive in nature. That is, electrodes as hereinafter explained, do not intrude into the path of the fluid flow. As shown, a test cell 150 is connected inline with line 23. Although the actual fittings are not shown, obviously test cell 150 includes means for being connected inline to line 23.

Test cell 150 may be basically made of metal except where noted otherwise. In this regard, test cell 150 includes four electrodes 152, 154, 156 and 157, mounted so that they are inline with the inner surface of line 23. As can be seen in FIG. 4, electrodes 152 through 157 are circular in nature and are in contact with the fluid passing through the meter. Electrodes 152 through 157 are separated from a metallic body 160 of test cell 150 by Teflon spacers 165 through 171. Teflon spacers 165 through 171 are concentric within Teflon body 180 which is contained within metal cylinder 185. Further, cylinder 185 has openings 190 which allow the electrical connections of 152 and 154 to excitation electronics 125 and also allows the connections of electrodes 156 and 157 to sensing electronics 130. Further, there are O-rings 195 between each interface of an insulator ring and an electrode and an insulator spacer and metallic body 160.

The operation of the second embodiment is the same as the first embodiment with the difference being that the injection current between electrodes 152 and 154 produces an electric field which is parallel to the fluid flow instead of perpendicular to the flow as in the first embodiment.

The temperature is sensed by a temperature sensor 137 as previously described for the other embodiment.

What is claimed is:
1. A water cut monitoring system comprising:
 accumulating means for accumulating a quantity of fluid from a producing well;
 removal means connected to the accumulating means for removing the fluid from the accumulating means as a stream of fluid after a predetermined time interval from the accumulation of the fluid by the accumulating means so as to allow the accumu- lated fluid to separate into three phases: free water, water-continuous and oil-continuous;

temperature means for sensing the temperature of the fluid stream and providing a temperature signal representative thereof; and water cut means including:

a plurality of electrodes means spatially arranged with the fluid stream, injection means connected to at least one electrode means for providing an AC injection voltage and an injection current to the fluid stream by way of the electrode means and providing an injection voltage signal and an injection current signal corresponding thereto, respectively, means for measuring the phase angle between the injection voltage and the injection current and providing a phase angle signal corresponding thereto, measuring means for measuring a voltage in the fluid stream and providing a measured voltage signal corresponding thereto, and means connected to the temperature sensing means, to the injection means and to the measuring means for determining the water cut of the fluid stream in accordance with the temperature signal, the injection voltage signal, the injection current signal, the measured voltage signal, and the phase angle signal.

2. A system as described in claim in which the injection means provides the injection voltage to a first pair of electrode means of the plurality of electrode means so as to cause the injection current to flow through the petroleum stream from one electrode means to the other electrode means of the first pair of electrode means; and a test cell means adapted to be connected inline with the line carrying the fluid stream for maintaining the plurality of electrode means in spatial arrangement with the fluid stream, voltage sensing means connected to a second pair of electrode means spatially arranged with said first pair of electrode means for sensing a voltage in the fluid stream across the second pair of electrode means, and network means connected to the injection means and to the plurality of electrode means for providing a water cut signal corresponding to the water cut of the fluid stream in accordance with the injection voltage, the injection current, the sensed voltage and the phase angle signal between the injection voltage and the injection current.

3. A system as described in claim 2 in which the network means includes:

means for deriving the injection impedance Zi in accordance with the injection voltage signal and the injection current signal, and first means for determining the water cut signal when the fluid is in the oil-continuous phase in accordance with the following equation:

$$WC = F + G(Zi) + H(Zipl)^2,$$

where F, G and H are empirically determined coefficients.

4. A system as described in claim 3 in which the network means includes:

means for determining the impedance of the fluid contacting the electrodes and providing a sensed impedance signal corresponding thereto, means for correcting the determined impedance signal in accordance with the sensed temperature, and means for determining an impedance ratio between free water impedance and the temperature corrected impedance where the free water impedance may be sensed or predetermined.

5. A system as described in claim 4 in which the network means includes the means for determining the impedance ratio in accordance with the following equation:

$$Zrat = (Zscor)/(Zwtr),$$

where Zrat is the impedance ratio, Zscor is the temperature corrected impedance and Zwtr is the impedance of free water.

6. A system as described in claim 5 in which the network means determines the water cut WC in accordance with the following equation:

$$WC = A + B(Zrat) + C(Zrat)^2 + D(Zrat)^3 + E(Zrat)^4,$$

where A, B, C, D and E are coefficients.

7. A system as described in claim 6 in which the second pair of electrode means are located between the two electrode means of the first pair of electrode means.

8. A system as described in claim 7 further comprising:

flow rate means connected to the removal means for measuring the flow rate of the fluid stream and providing a flow rate signal corresponding thereto, and means connected to the water cut means and to the flow rate means for determining the total oil content and/or the total water content of the fluid that was accumulated by the accumulating means in accordance with the flow rate signal and the water cut signal.

9. A system as described in claim 8 in which the injection means provides the injection voltage at a frequency lying within a range of frequencies from 1 MHz to 50 MHz.

10. A system as described in claim 1 further comprising:

flow rate means connected to the removal means for measuring the flow rate of the fluid stream and providing a flow rate signal corresponding thereto, and means connected to the water cut means and to the flow rate means for determining the total oil content and/or the total water content of the fluid that was accumulated by the accumulating means in accordance with the flow rate signal and the water cut signal.

11. A water cut monitor comprising:

a test cell connected to ground and adapted to be connected inline with a line carrying a fluid stream, a plurality of electrode means contained in the test cell spatially arranged so the electrodes means are in contact with the fluid stream, injection means for providing an AC injection voltage at a predetermined frequency across a first electrode means of the plurality of electrode means and ground so as to cause an injection current to flow through the petroleum stream from the first electrode means to ground, means connected to a pair of electrode means spatially arranged with said first electrode means and ground for sensing a voltage in a petroleum stream across the second pair of electrode means, output means connected to the injection means and to the plurality of electrode means for providing outputs corresponding to the injection voltage, the injection current, the sensed voltage and the phase difference between the injection voltage and the injection current, and means for providing a signal corresponding to the water cut of the petroleum stream in accordance with the outputs from the output means.

12. A monitor as described in claim 11 in which the water cut means further includes:

first means for determining the water cut of the fluid when the fluid is in the oil-continuous phase in accordance with the following equation:

$$WC = F + G (Zi) + H (Zi)^2$$

where F, G and H are empirically determined coefficients.

13. A monitor as described in claim 12 in which the water cut means includes:

means for determining the impedance of the fluid contacting the electrodes and providing a sensed impedance signal, and means for correcting the determined impedance signal in accordance with the sensed temperature, means for determining the impedance ratio between free water impedance and the temperature corrected impedance where the free water impedance may be the sensed impedance or a predetermined impedance.

14. A monitor as described in claim 13 in which the water cut means includes the means for determining the impedance ratio in accordance with the following equation:

$$Zrat = (Zscor)/(Zwtr),$$

where Zrat is the impedance ratio, Zscor is the temperature corrected impedance and Zwtr is the impedance of free water.

15. A monitor as described in claim 14 in which the water cut means determines the water cut WC in accordance with the following equation:

$$WC = A + B (Zrat) + C (Zrat)^2 + D (Zrat)^3 + E (Zrat)^4,$$

where A, B, C, D and E are coefficients.

16. A monitor as described in claim 15 in which the second pair of electrode means are located between the two electrode means of the first pair of electrode means.

17. A monitor as described in claim 16 in which the injection means provides the injection voltage at a frequency lying within a range of frequencies from 1 MHz to 50 MHz.

18. A monitor as described in claim 17 further comprising:

flow rate means connected to the removal means for measuring the flow rate of the fluid stream and providing a flow rate signal corresponding thereto, and means connected to the water cut means and to the flow rate means for determining the total oil content and/or the total water content of the fluid that was accumulated by the accumulating means in accordance with the flow rate signal and the water cut signal.

19. A water cut monitor comprising:

a test cell connected to ground and adapted to be connected inline with a line carrying a petroleum stream and a rectangular cross-sectional area, at least three electrodes located within a test cell and in the petroleum stream, means for providing an AC injection voltage having a preferred frequency range across a first electrode and ground so as to cause an injection current to flow through the petroleum stream from the first electrode to ground, means connected to a second and a third electrode spatially arranged between the first electrode and ground for sensing a voltage in a petroleum stream across the second and third electrodes, output means connected to the electrodes for providing outputs corresponding to the injection voltage, the injection current, the sensed voltage and the phase difference between the injection voltage and the injection current, and means for providing a signal corresponding to the water cut of the petroleum stream in accordance with the outputs from the output means.

20. A monitor as described in claim 19 in which the water cut means further includes:

first means for determining the water cut of the fluid when the fluid is in the oil-continuous phase in accordance with the following equation:

$$WC = F + G (Zi) + H (Zi)^2$$

where F, G and H are empirically determined coefficients.

21. A monitor as described in claim 20 in which the water cut means includes:

means for determining the impedance of the fluid, contacting the electrodes and providing a sensed impedance signal, means for correcting the determined impedance signal in accordance with the sensed temperature, and means for determining an impedance ratio between free water impedance and the temperature corrected impedance where the free water impedance may be either the sensed impedance or a predetermined impedance.

22. A monitor as described in claim 21 in which the water cut means includes the means for determining the impedance ratio in accordance with the following equation:

$$Zrat = (Zscor)/(Zwtr),$$

where Zrat is the impedance ratio, Zscor is the temperature corrected impedance and Zwtr is the impedance of free water.

23. A monitor as described in claim 22 in which the water cut means determines the water cut WC in accordance with the following equation:

$$WC = A + B (Zrat) + C (Zrat)^2 + D (Zrat)^3 + E (Zrat)^4,$$

where A, B, C, D and E are coefficients.

24. A monitor as described in claim 23 in which the injection means provides the injection voltage at a frequency lying within a range of frequencies from 1 MHz to 50 MHz.

25. A water cut monitoring method comprising the steps of:
   accumulating a quantity of fluid from a producing well in an accumulating means;
   removing the fluid from the accumulating means as a stream of fluid after a predetermined time interval, so as to allow the accumulated fluid to separate into three phases: free water, water-continuous and oil-continuous;
   sensing the temperature of the fluid stream,
   providing a temperature signal representative of the sensed temperature, and
   placing a plurality of electrode means in spatial arrangement with the fluid stream,
   providing an AC injection voltage and an injection current to the fluid stream by way of at least one pair of electrode means,
   providing an injection voltage signal and an injection current signal corresponding to the injection voltage and the injection current, respectively,
   measuring the phase angle between the injection voltage and the injection current,
   providing a phase angle signal corresponding to the measured phase angle,
   measuring a voltage in the fluid stream,
   providing a measured voltage signal corresponding to the measured voltage, and
   determining the water cut of the fluid stream in accordance with the temperature signal, the injection voltage signal, the injection current signal, the measured voltage signal, and the phase angle signal.

26. A method as described in claim 25 in which the injecting step includes:
   providing the injection voltage to a first pair of electrode means of the plurality of electrode means so as to cause the injection current to flow through the petroleum stream from one electrode means to the other electrode means of the first pair of electrode means; and
   using a test cell means adapted to be connected inline with the line carrying the fluid stream for maintaining the plurality of electrode means in spatial arrangement with the fluid stream;
   the voltage sensing step includes:
   sensing a voltage in the fluid stream across a second pair of electrode means; and
   the determining step includes:
   providing a water cut signal corresponding to the water cut of the petroleum stream in accordance with the injection voltage signal, the injection current signal, the sensed voltage signal and the phase angle signal.

27. A method as described in claim 26 in which the water cut signal step includes:
   determining the injection impedance Zi in accordance with the injection voltage signal and the injection current signal, and
   providing the water cut signal, when the fluid is in the oil-continuous phase, in accordance with the following equation:

$$WC = F + G(Zi) + H(Zi)^2,$$

where F, G and H are coefficients.

28. A method as described in claim 27 in which the water cut signal step includes:
   determining the impedance of the fluid contacting the electrodes,
   correcting the determined impedance signal in accordance with the sensed temperature, and
   determining an impedance ratio between free water impedance and the temperature corrected impedance where the free water impedance may be either measured or predetermined.

29. A method as described in claim 28 in which the water cut signal step includes:
   determining the impedance ratio in accordance with the following equation:

$$Zrat = (Zscor)/(Zwtr),$$

where Zrat is the impedance ratio, Zscor is the temperature corrected impedance and Zwtr is the impedance of free water.

30. A method as described in claim 29 in which the water cut signal step includes:
   providing the water cut signal, when the fluid is in the water-continuous phase, in accordance with the following equation:

$$WC = A + B(Zrat) + C(Zrat)^2 + D(Zrat)^3 + E(Zrat)^4,$$

where A, Bm, C, D and E are coefficients.

31. A method as described in claim 30 in which the injection means provides the injection voltage at a frequency lying within a range of frequencies from 1 MHz to 50 MHz.

32. A system as described in claim 31 further comprising the steps of:
   measuring the flow rate of the fluid stream,
   providing a flow rate signal corresponding to the measured flow rate, and
   determining the total oil content and/or the total water content of the fluid that was accumulated by the accumulating means in accordance with the flow rate signal and the water cut signal.

* * * * *